United States Patent
Kumar et al.

(10) Patent No.: US 7,078,534 B2
(45) Date of Patent: Jul. 18, 2006

(54) PROCESS FOR THE PREPARATION OF CRYSTALLINE N-FORMIMIDOYL THIENAMYCIN MONOHYDRATE (IMIPENEM MONOHYDRATE)

(75) Inventors: Yatendra Kumar, Haryana (IN); Neera Tewari, Haryana (IN); Ran Chander Aryan, Delhi (IN); Bishwa Prakash Rai, Uttar Pradesh (IN); Seema Ahuja, Uttar Pradesh (IN)

(73) Assignee: Ranbaxy Laboratories Limited, Haryana (IN)

( * ) Notice: Subject to any disclaimer, the term of this patent is extended or adjusted under 35 U.S.C. 154(b) by 0 days.

(21) Appl. No.: 10/415,633

(22) PCT Filed: Nov. 5, 2001

(86) PCT No.: PCT/IB01/02069

§ 371 (c)(1),
(2), (4) Date: Sep. 18, 2003

(87) PCT Pub. No.: WO02/36594

PCT Pub. Date: May 10, 2002

(65) Prior Publication Data

US 2004/0054167 A1    Mar. 18, 2004

(30) Foreign Application Priority Data

Nov. 3, 2000    (IN) .......................... 983/DEL/2000

(51) Int. Cl.
*C07D 209/32*    (2006.01)
(52) U.S. Cl. ...................................................... 548/512
(58) Field of Classification Search ................. 548/512
See application file for complete search history.

(56) References Cited

U.S. PATENT DOCUMENTS

| | | | |
|---|---|---|---|
| 4,194,047 A | 3/1980 | Christensen et al. | 546/272 |
| 4,260,543 A | 4/1981 | Miller | 260/245.2 T |
| 5,245,069 A * | 9/1993 | McManus | 558/148 |
| 5,872,250 A | 2/1999 | Williams et al. | 540/350 |

FOREIGN PATENT DOCUMENTS

| | | |
|---|---|---|
| RU | 2 070 555 | 12/1996 |
| RU | 2 091 381 | 9/1997 |
| RU | 2 130 938 | 5/1999 |

OTHER PUBLICATIONS

Nicholas D. Cheronis, 1958, "Semicro Experimental Organic Chemistry", Chapter 5.*
M. Connolly et al, *J. Pharm Sci.*; 84, 174-177 (1996).

* cited by examiner

*Primary Examiner*—Joseph K. McKane
*Assistant Examiner*—Robert Shiao
(74) *Attorney, Agent, or Firm*—Jayadeep R. Deshmukh, Esq.; George E. Heibel, Esq.

(57) ABSTRACT

The present invention relates to a cost effective and commercially viable process for the preparation of crystalline N-formimidoyl thienamycin monohydrate (Imipenem monohydrate) of Formula I.

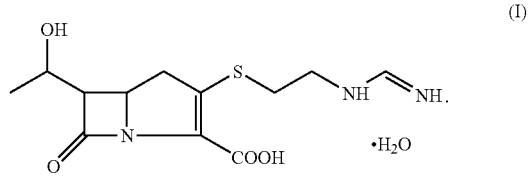

(I)

11 Claims, 1 Drawing Sheet

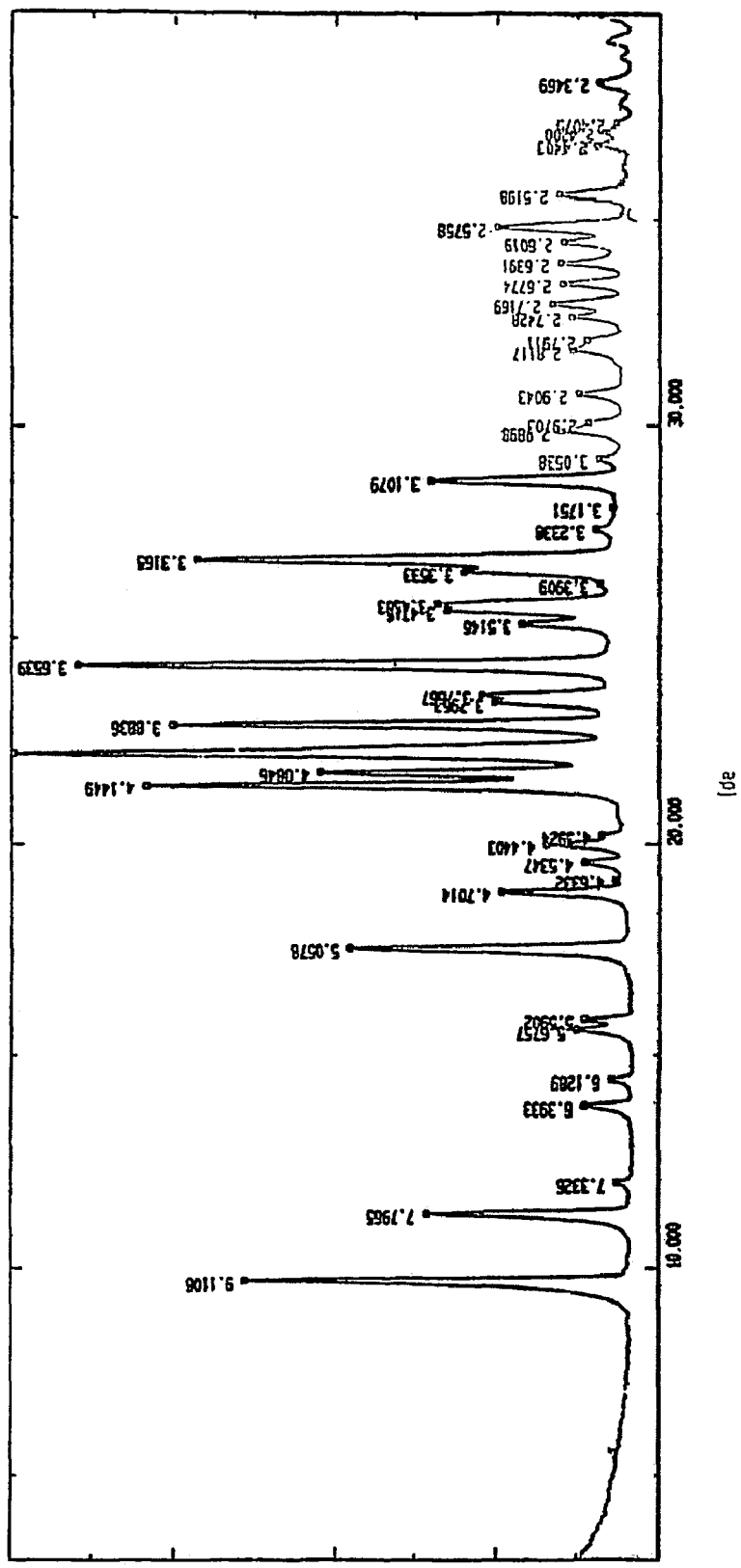

PROCESS FOR THE PREPARATION OF CRYSTALLINE N-FORMIMIDOYL THIENAMYCIN MONOHYDRATE (IMIPENEM MONOHYDRATE)

FIELD OF THE INVENTION

The present invention relates to a cost effective and commercially viable process for the preparation of crystalline N-formimidoyl thienamycin monohydrate (Imipenem monohydrate) of Formula I:

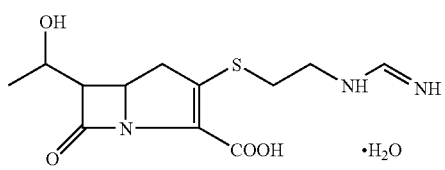

FORMULA I

BACKGROUND OF THE INVENTION

Imipenem monohydrate, the crystalline monohydrate of N-formimidoyl derivative of thienamycin of Formula I, is the first clinically available member of a new class of β-lactam antibiotic that possess the carbapenem ring system. Imipenem exhibits an extremely broad spectrum of activity against gram-positive and gram-negative aerobic and anaerobic species, which is partly due to its high stability in presence of β-lactamases.

Imipenem was initially obtained by lyophilization technique as disclosed in U.S. Pat. No. 4,194,047. An alternate process of freeze crystallization or lyophilization has been reported by M. Connolly et. al in J. Pharm. Sci, 85, 174–175 (1996). However, lyophilized product so obtained is often found to be largely amorphous which is thermodynamically unstable. A crystalline monohydrate form of imipenem is disclosed in U.S. Pat. No. 4,260,543, which is obtained by crystallization of a lyophilized sample of imipenem and was found to have unexpected stability in the solid state over the lyophilized form (amorphous form). However, it is reported that the changes in lyophilization conditions can change the degree of crystallinity of the final product. Crystallinity is of interest in the study of lyophilized imipenem because crystalline imipenem is more thermodynamically stable than amorphous or disordered imipenem. Processes of obtaining crystalline imipenem as described in the prior art requires specialized equipment such as freeze dryer or a lyophilizer which renders it unattractive at a commercial scale and also do not produce the product having consistent degree of crystallinity.

SUMMARY OF THE INVENTION

It is an object of the present invention to provide a cost effective and commercially viable process for producing highly pure thermally stable crystalline imipenem monohydrate having uniform degree of crystallinity directly from an aqueous solution obtained from the reaction mixture without involving lyophilization at any stage.

More particularly, the present invention relates to a process for the preparation of crystalline N-formimidoyl thienamycin monohydrate (imipenem monohydrate) of Formula I which comprises (a) activating a keto ester compound of Formula II

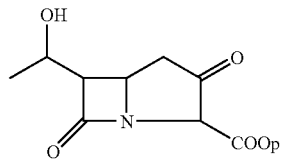

FORMULA II wherein p is hydrogen or a protecting group, in the presence of a suitable secondary amine, in a suitable N-substituted lactam or N,N-disubstituted amide as a solvent, optionally in combination with an inert organic solvent to obtain an activated keto ester of Formula III

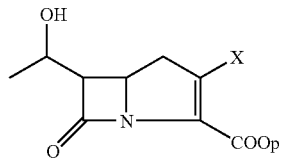

FORMULA III wherein X is $OP(O)(OR)_2$ or $OS(O)_2R$ and R is $C_{1-6}$ alkyl, $C_{1-6}$ alkaryl, aryl or perfluoro $C_{1-6}$ alkyl. The term alkyl refers to a straight or branched chain and when of sufficient size, may be cyclic. Preferred straight or branched alkyl groups include methyl, ethyl, propyl, isopropyl, butyl and t-butyl. Preferred cycloalkyl groups include cyclopropyl, cyclopentyl, cyclohexyl and cyclopropyl methyl. The term aryl refers to aromatic rings including phenyl, substituted phenyl and naphthyl. Aryl groups may be substituted with one to three substitutents independently selected from a halogen, alkyl and halogenated lower alkyl group, wherein alkyl has the same meaning as defined above.

The protecting group p may be any of the readily removable carboxyl protecting groups. Preferably, p can be selected from the group consisting of benzyl, p-nitrobenzyl and methoxymethyl.

The suitable secondary amine is selected from the group consisting of diisopropylamine, dicyclohexylamine, 2,2,6,6-tetramethylethyl piperidine (TMP) and 1,1,3,3-tetramethylguanide (TMG).

The suitable N-substituted lactam is selected from the group consisting of N-methyl-pyrrolidone (NMP), N-ethyl-pyrrolidone (NEP), N-methyl piperidinone and 1,3-dimethyl 3,4,5,6-tetrahydro-2(H) pyrimidinone (DMPH). The suitable N,N-disubstituted amide is selected from the group consisting of dimethylformamide (DMF), dimethylacetamide (DMAc) and optional inert organic solvent is preferably tetrahydrofuran. The reaction is carried out at a temperature ranging between –20 to –70° C. The compound of Formula II may be prepared using methods known in the art.

(b) Reacting the activated keto ester of Formula III, in situ with 2-aminoethanethiol (cysteamine) or with its salt in the presence of a secondary amine in N-substituted lactam or N, N-disubstituted amide at a temperature ranging from –80° C. to –40° C. to get thienamycin ester of Formula IV

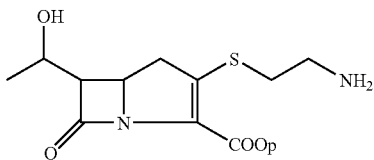

FORMULA IV wherein p,N-substituted lactam and N,N-disubstituted amine have the same meanings as defined above.

(c) Reacting thienamycin ester of Formula IV, in situ with benzyl formimidate hydrochloride ($C_6H_5CH_2OCH=NH_2^+Cl^-$) in the presence of a secondary amine in N-substituted lactam or N,N-disubstituted amide to get amidine carboxylate ester (blocked N-formimidoyl thienamycin) of Formula V

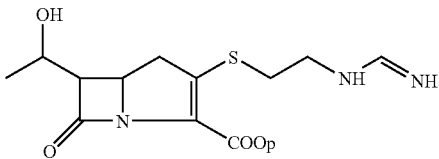

FORMULA V wherein p,N-substituted lactam and N,N-disubstituted amide have the same meanings as defined above.

(d) Hydrogenation of the blocked N-formimidoyl thienamycin of Formula V to get imipenem and the solution containing the reaction mixture is subjected to dianion chromatography, followed by crystallization in the presence of a suitable alcohol or a ketone as a co-solvent to yield highly pure crystalline N-formimidoyl thienamycin monohydrate (imipenem monohydrate). Suitable alcohol and ketone may be selected from ethanol, isopropanol, acetone and methyl isobutyl ketone.

DETAILED DESCRIPTION OF THE INVENTION

In the following section one preferred embodiment is described by way of example to illustrate the process of this invention. However, these are not intended in any way to limit the scope of the present invention.

EXAMPLE 1

Preparation of Crytalline Imipenem Monohydrate

Step 1—Preparation of (5R, 6S) p-Nitrobenzyl-3-(diphenylphosphono)-6-[(1R)-1-hydroxyethyl]-1-azabicyclo [3.2.0] hept-2-ene-7-one-2-carboxylate To a solution of p-nitrobenzyl (5R, 6S)p-Nitrobenzyl-6 [(1R)-1-hydroxyethyl]-1-azabicyclo[3.2.0]-heptan-3,7-dione-2-carboxylate (20.0 g, 57 mmol) in a mixture of tetrahydrofuran and 1,3-dimethyl-3,4,5,6-tetrahydro (2H) pyrimidinone (160 ml; 1:1 v/v) was added diisopropylamine (7.0 g, 69 mmol) at −25 to −30° C. followed by diphenyl-chlorophosphate (17.0 g, 63 mmol). The mixture was stirred for 40–45 min. at −10 to −15° C. and used in the next step without isolation of the enol phosphate intermediate.

Step II—Preparation of (5R,6S) p-Nitrobenzyl-3-[(2-aminoethyl)thio]-6-[(1R)-1-hydroxyethyl]-1-azabicyclo [3.2.0] hept-2-ene-7-one-2-carboxylate The reaction mixture from Step I was cooled to −75° C. A solution of cysteamine (2-aminoethanethiol) hydrochloride (7.2 g, 63 mmol) in 1,3-dimethyl-3,4,5,6-tetrahydro (2H) pyrimidinone (70 ml) and diisopropylamine (7.0 g, 69 mmol) was added at −75 to −50° C. in 10 min. The reaction mixture thus obtained was further stirred at −40° C. to −45° C. for about 1 hr and was used as such without its isolation.

Step III—Preparation of (5R,6S) p-Nitrobenzyl-3-[2-[(iminomethyl)amino]ethyl]thio]-6-[(1 R)-1-hydroxyethyl]-1-azabicyclo[3.2.0]hept-2-ene-7-one-2-carboxylate The reaction mixture from Step II was cooled to −45° C., and diisopropylamine (8.7 g, 86 mmol) was added followed by benzylformimidate hydrochloride (12.8 g, 74.6 mmol). The resulting mixture was stirred at −45 to −40° C. for about 30 minutes and then at −20 to −15° C. for about 1 hour 30 minutes. Tetrahydrofuran (200 ml) was added at −20 to −15° C. and diisopropylamine salts were filtered off from the reaction mixture. The filtrate contained the N-formamidoyl thienamycin PNB ester.

Step IV—Preparation of [5R-[5α, 6α(R*)]]-6-(1-hydroxyethyl)-3-[[2-[(iminomethyl)amino]ethyl]thio]-7-oxo-1-azabicylo[3.2.0]hept-2-ene-2-carboxylic acid The filtrate from Step III containing PNB-N-formimidoyl thienamycin was poured into a mixture of water (400 ml), N-methylmorpholine (18 g), isopropyl alcohol (200 ml) at 0–5° C. and at pH of about 7.0. The reaction mixture was then hydrogenated over at 3–4 kg of hydrogen pressure at 5–10° C. The reaction mixture was filtered, extracted with methylene chloride (2×300 ml) and the aqueous layer was separated. The aqueous layer was concentrated to 200 ml by distillation under reduced pressure. The concentrated solution was purified by dianion chromatography using water as an eluent. The fractions containing the desired product were combined and concentrated either under reduced pressure or using plain membrane type reverse osmosis techniques to a volume of 50 ml. The concentrated solution was then cooled to 0–5° C. and isopropyl alcohol (25 ml) was added to it. It was further stirred for 40–45 min at the same temperature. Another lot of isopropyl alcohol (25 ml) was added and stirring continued for about 1 hour at 0–5° C. The crystalline precipitate obtained was filtered, washed with isopropyl alcohol and acetone (2×10 ml) and dried to yield 4.0 g of crystalline N-formimidoyl thienamycin.

X-ray diffraction pattern (FIG. 1) shows peaks characteristic of crystalline form of imipenem monohydrate as obtained per U.S. Pat. No. 4,260,543; Purity by HPLC=99.23%.

While the present invention has been described in terms of its specific embodiments, certain modifications and equivalents will be apparent to those skilled in the art and are intended to be included within the scope of the present invention.

What is claimed is:

1. A process for the preparation and isolation of highly pure crystalline N-formimidoyl thienamycin monohydrate (imipenem) of Formula I having the X-ray diffraction pattern having characteristic d-spacing values at about 9.11, 7.79, 5.05, 4.14, 4.08, 3.90, 3.88, 3.65, 3.31, and 3.10, directly from a reaction mixture without any need to prepare lyophilized imipenem first, the process comprising:

FORMULA I

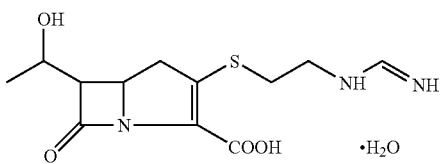

(a) activating a keto ester compound of Formula II

FORMULA II

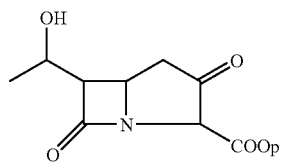

wherein p is hydrogen or a protecting group, in the presence of a suitable secondary amine, in a suitable N-substituted lactam or N,N-disubstituted amide as a solvent, optionally in combination with an inert organic solvent to obtain a compound of Formula III

FORMULA III

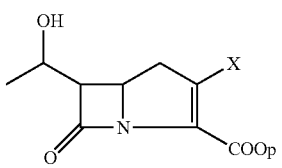

wherein x is $OP(O)(OR)_2$ or $OS(O)_2 R$ and R is $C_{1-6}$ alkyl, $C_{1-6}$ alkaryl, aryl or perfluoro $C_{1-6}$ alkyl; the term alkyl refers to a straight or branched chain and when of sufficient size, may be cyclic, preferred straight or branched alkyl groups include methyl, ethyl, propyl, isopropyl, butyl and t-butyl, preferred cycloalkyl groups include cyclopropyl, cyclopentyl, cyclohexyl and cyclopropyl methyl; the term aryl refers to aromatic rings including phenyl, substituted phenyl and naphthyl, aryl groups may be substituted with one to three substituents independently selected from halogen, alkyl and halogenated lower alkyl group, wherein alkyl has the same meaning as defined above, (b) reacting the activated keto ester of Formula III in situ with 2-aminoethanethiol (cysteamine) or its salt in the presence of a secondary amine, in a N-substituted lactam or N,N-disubstituted amide as a solvent to get thienamycin ester of Formula IV

FORMULA IV

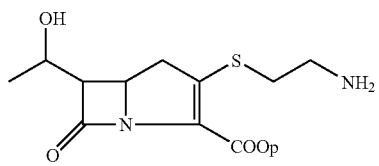

wherein p,n-substituted lactam and N,N-disubstituted amine, have the same meaning as defined above, (c) reacting thienamycin ester of Formula IV, in situ with benzyl formimidate hydrochloride $(C^6H_5CH_2OCH=NH_2{}^{30}\ Cl^-)$ in the presence of a secondary amine in (d) a N-substituted lactam or N,N-disubstituted amide to get amidine carboxylate ester (blocked N-formimidoyl thienamycin) of Formula V

FORMULA V

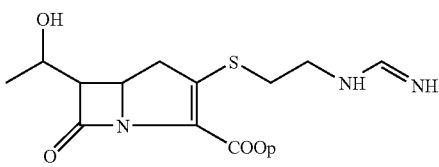

wherein p,N-substituted lactam and N,N-disubstituted amine, have the same meaning as defined above, and (e) hydrogenating the blocked N-formimidoyl thienamycin of Formula V, to yield N-formimidoyl thienamycin (imipenem) in a solution and subjecting the solution containing the imipenem to dianion chromatography followed by crystallization in the presence of an alcohol or a ketone co-solvent, and isolating the highly pure crystalline N-formimidoyl monohydrate (imipenem monohydrate) of Formula I, by filtration.

2. The process of claim 1 wherein the protecting group p is selected from the group consisting of benzyl, p-nitrobenzyl and methoxymethyl.

3. The process of claim 1 wherein the suitable secondary amine is selected from the group consisting of diisopropylamine, dicyclohexyl amine, 2,2,6,6-tetramethylethyl piperidine (TMP) and 1,1,3,3-tetramethylguanide (TMG).

4. The process of claim 1 wherein the N-substituted lactam or N,N-disubstituted amide is used alone or in combination with an inert solvent.

5. The process in accordance with claim 4 wherein the N-substituted lactam is selected from the group consisting of N-methyl pyrrolidone (NMP), N-ethylpyrrolidone (NEP), N-methylpiperidone and 1,3-dimethyl-3,4,5,6-tetrahydro (2H) pyrimidinone.

6. The process in accordance with claim 4 wherein the suitable N,N-disubstituted amide is selected from the group consisting of dimethylformamide (DMF) and dimethylacetamide (DMAc).

7. The process of claim 4 wherein the inert solvent is tetrahydrofuran.

8. The process of claim 4 wherein a mixture of 1,3-dimethyl-3,4,5,6-tetrahydro-2(H) pyrimidinone and tetrahydrofuran is used as a solvent.

9. The process according to claim 1 wherein the alcohol is selected from the group consisting of ethanol and isopropyl alcohol.

10. The process according to claim 1 wherein the ketone is selected from the group consisting of acetone and methyl isobutyl ketone.

11. The process of claim 1 wherein the highly pure crystalline N-formimidoyl thienamycin monohydrate (imipenem) has a purity of more than 99% by HPLC.

* * * * *

UNITED STATES PATENT AND TRADEMARK OFFICE
CERTIFICATE OF CORRECTION

PATENT NO.        : 7,078,534 B2                                              Page 1 of 1
APPLICATION NO. : 10/415633
DATED             : July 18, 2006
INVENTOR(S)       : Kumar et al.

It is certified that error appears in the above-identified patent and that said Letters Patent is hereby corrected as shown below:

Front page, Inventor section: "Ran" should read --Ram--
Column 5, Line 39, "$C_{16}$" should read --$C_{1-6}$--
Column 6, Line 5, "$C^6$" should read --$C_6$--
Column 6, Line 5, "$NH_2^{30}Cl^-$" should read --$NH_2^+Cl^-$--

Signed and Sealed this

Twentieth Day of November, 2007

JON W. DUDAS
*Director of the United States Patent and Trademark Office*